United States Patent
Simmons et al.

(10) Patent No.: US 9,895,446 B2
(45) Date of Patent: Feb. 20, 2018

(54) POLOXAMER-BASED INTRALESIONAL INJECTIONS FOR THE DELIVERY OF CHEMOTHERAPEUTIC AGENTS

(71) Applicants: PROFESSIONAL COMPOUNDING CENTERS OF AMERICA (PCCA) (50% INTEREST), Houston, TX (US); BEST PET RX IP, INC. (50% INTEREST), New York, NY (US)

(72) Inventors: Chris V. Simmons, Sugar Land, TX (US); Danny Carrero, New York, NY (US)

(73) Assignees: Professional Compounding Centers of America, Houston, TX (US); Best Pet Rx IP, Inc., New York, NY (US)

( * ) Notice: Subject to any disclaimer, the term of this patent is extended or adjusted under 35 U.S.C. 154(b) by 0 days.

(21) Appl. No.: 15/210,632

(22) Filed: Jul. 14, 2016

(65) Prior Publication Data

US 2017/0014514 A1 Jan. 19, 2017

Related U.S. Application Data

(60) Provisional application No. 62/192,442, filed on Jul. 14, 2015.

(51) Int. Cl.

| | | |
|---|---|---|
| *A61K 31/4965* | (2006.01) | |
| *A61K 31/28* | (2006.01) | |
| *A61K 31/17* | (2006.01) | |
| *A61K 31/13* | (2006.01) | |
| *A61K 47/34* | (2017.01) | |
| *A61K 9/00* | (2006.01) | |
| *A61K 9/08* | (2006.01) | |
| *A61K 31/555* | (2006.01) | |

(52) U.S. Cl.
CPC ............ *A61K 47/34* (2013.01); *A61K 9/0024* (2013.01); *A61K 9/08* (2013.01); *A61K 31/555* (2013.01)

(58) Field of Classification Search
CPC ...... C07D 401/12; A61K 31/28; A61K 31/17; A61K 31/13
USPC ............................ 514/255.05, 492, 588, 663
See application file for complete search history.

(56) References Cited

U.S. PATENT DOCUMENTS

2006/0013883 A1 1/2006 Nicol et al.
2012/0308616 A1 12/2012 Liu et al.

FOREIGN PATENT DOCUMENTS

| EP | 2111867 A1 | 10/2009 |
|---|---|---|
| GB | 1612274.9 | 5/2017 |
| WO | 199821228 | 5/1998 |
| WO | 200132218 A1 | 5/2001 |
| WO | 2010088924 A1 | 8/2010 |
| WO | 2011112900 A2 | 9/2011 |

*Primary Examiner* — Raymond J Henley, III
(74) *Attorney, Agent, or Firm* — David G. Woodral; Scott R. Zingerman; Gable Gotwals

(57) ABSTRACT

Intralesional injections including poloxamer compounds and anticancer drugs are disclosed. The combination of the poloxamer-based composition with chemotherapeutic agents within the disclosed intralesional injections provides a synergistic effect, thereby allowing lower dosages of the active drugs and enhancing the treatment effectiveness. The disclosed poloxamer-based intralesional injections are employed for treating different types of cancer in humans and other animal species. The disclosed intralesional injections can be used as the sole therapy or in combination with one or more additional therapies, such as, chemotherapy, electrotherapy, immunotherapy and/or radiation therapy. The disclosed intralesional injections can be employed in virotherapy and gene therapy treatments. The disclosed intralesional injections are designed for immediate release or controlled release of the active drugs. The disclosed intralesional injections are employed for local or systemic administration of active drugs.

20 Claims, No Drawings

POLOXAMER-BASED INTRALESIONAL INJECTIONS FOR THE DELIVERY OF CHEMOTHERAPEUTIC AGENTS

CROSS-REFERENCE TO RELATED CASES

This application claims the benefit of U.S. provisional patent application Ser. No. 62/192,442, filed on Jul. 14, 2015, and incorporates such provisional application by reference into this disclosure as if fully set out at this point.

FIELD OF THE INVENTION

The present disclosure relates generally to pharmaceutical compositions, and more particularly, to intralesional injections including poloxamer compounds for treating cancer.

BACKGROUND OF THE INVENTION

Cancer is an uncontrolled growth of abnormal cells on or within the body of humans and animals. Cancer may be benign or malignant, and malignancies may be localized or may invade adjacent tissue and spread throughout the body of the subject. There are many types of malignant cancer including lung cancer, blood cancer, brain cancer, perianal gland adenoma, squamous cell carcinoma, and the like. The incidence of cancer in companion animals, such as, for example dogs, cats and the like is increasing, and cancer is now considered to be the leading cause of death in older animals. It is believed that the annual incidence rate for cancer in dogs is about 2 to 2.5% (about the same as humans) and about 1.5 to 2% for cats.

Several studies suggest that the cancer having the highest incidence in animals (e.g., companion animals, reptiles, and birds) are mast cell tumor (16.8%), lipoma (8.5%), histiocytoma (8.4%), perianal gland adenoma (7.8%), sebaceous gland hyperplasia adenoma (6.5%), and squamous cell carcinoma (6.0%), among others. Some of the aforementioned cancers are benign and some are malignant. Unfortunately, benign tumors can be as dangerous as malignant growths if they are allowed to grow to a point where they prevent normal bodily function. Additionally, benign tumors have the potential to become malignant through a process known as tumor progression.

Generally, veterinary oncologists have "off-label" drug use privileges. Off-label drug use means that the veterinary oncologists can use drugs approved for one species (including humans) freely in another species. Currently, veterinary oncologists tend to select chemotherapeutics exhibiting significant positive results in human oncology for treating cancer in animals.

Chemotherapeutic agents are typically systemically delivered and may reduce tumor bulk and delay metastasis, but there is a profound morbidity associated with this type of treatment. Despite the many disadvantages and side effects of employing these strongly cytotoxic drugs, chemotherapeutic agents have found extensive use due to the positive anti-carcinogenic results experienced. Because of the side effects associated with the systemic delivery of chemotherapeutic agents, there is a substantial interest in delivering chemotherapeutic agents in a manner which directs their activity toward the abnormal cells. This activity toward the abnormal cells would avoid the exposure of sensitive normal cells to the cytotoxic effects of the drugs, both in the vicinity of and distant from the abnormal cell growth.

Localized chemotherapy treatments (e.g., intralesional injections) direct the anti-cancer drugs into the part of the body where the cancer is located, thereby allowing higher concentration of the drugs at the administration site and further minimizing the side effects in patients. However, side effects still occur since the drugs can be absorbed into the bloodstream and travel throughout the body due to the inability of current injection preparations to remain at the site of contact and only target the cancer cells. Some drawbacks associated with chemotherapy treatments include: limited use at certain stages of the disease; chemotherapeutic drugs cannot distinguish between malignant cancer cells and normal cells; and toxicity to normal, healthy, rapidly growing or self-renewing tissues within the body.

Therefore, there is a need for a pharmaceutical composition including chemotherapeutic agents that are non-systemically delivered and do not possess the limitations listed immediately above.

SUMMARY OF THE INVENTION

There is a need for cancer treatments possessing fewer side effects and exhibiting the property of efficiently targeting only the cancer cells. The present invention is directed to less toxic and more efficient treatments for the following cancers: carcinoma, such as, for example, squamous cell carcinoma, adenocarcinoma, adenosquamous carcinoma, anaplastic carcinoma, large cell carcinoma, small cell carcinoma, among others; as well as other types of cancer, such as, for example, mast cell tumor, lipoma, histiocytoma, perianal gland adenoma, sebaceous gland hyperplasia adenoma, and the like.

In some embodiments, intralesional injections for the treatment of cancer are disclosed. In these embodiments, the intralesional injections include at least one chemotherapeutic agent as the API within a poloxamer-based composition. Further to these embodiments, the poloxamer-based composition employed as the therapeutic vehicle includes one or more poloxamers having different molecular weights. In these embodiments, the intralesional injections include different/additional components, such as, a solvent (e.g., distilled water), among others. Further to these embodiments, the combination of the poloxamer-based composition with the chemotherapeutic agents provides a synergistic effect due to the multiple molecular weight poloxamers attraction to cells possessing abnormal membrane structures. This synergistic effect allows lower dosages of the APIs, an improved chemosensitization of cancer cells, and an increase in the cytotoxic activity of the chemotherapeutic agents on the cancer cells.

In some embodiments, the disclosed poloxamer-based intralesional injections are employed for treating a plurality of cancer in humans and animals. In these embodiments, the poloxamer-based intralesional injections can be used to effectively reduce the size of carcinomas or tumors. Further to these embodiments, the poloxamer-based injections are used to eliminate cancer from a patient.

In some embodiments, the poloxamer-based intralesional injections are applied directly into a carcinoma or tumor of a patient suffering from cancer. In these embodiments, the local therapeutic effect of the poloxamer-based intralesional injections allows lower dosages of the APIs and provides higher concentrations of the APIs at the targeted site In some embodiments, the poloxamer-based intralesional injections are formulated to specifically target abnormal cells that are the cause of tumor formations or carcinomas in a patient. In these embodiments, the poloxamer vehicle within the injections is attracted to abnormal cells possessing different membrane structures than normal cells. Further to these embodiments, the poloxamer vehicle within the injections causes inhibition of the normal functioning of MDR proteins on the surface of abnormal cells. In these embodiments, the inhibition of the MDR proteins to function normally on the surface of the abnormal cells increases the effectiveness of chemotherapeutic agents in eliminating or reducing tumors and carcinomas.

In some embodiments, the poloxamer-based intralesional injections are administered alone as the sole therapeutic agent. In other embodiments, the poloxamer-based intralesional injections are used in combination with one or more additional therapies, such as, for example, radiation therapy, electrotherapy, and immunotherapy, among others.

In some embodiments, the poloxamer-based intralesional injections enable an efficient administration of the APIs, such as, for example, chemotherapeutic agents, thereby improving the safety and effectiveness of the treatment. In these embodiments, the poloxamer-based intralesional injections are used for localized delivery of the APIs. Further to these embodiments, the poloxamer-based intralesional injections allow the delivery of chemotherapeutic agents directly at the target site, such as, for example tumors or carcinomas of a patient, thereby resulting in a higher concentration of the APIs at the target site. In other embodiments, the poloxamer-based intralesional injections are used for systemic delivery of the APIs. In these embodiments, the poloxamer-based intralesional injections allow the delivery of chemotherapeutic agents to the systemic circulation, thereby resulting in a higher percentage of bioavailability of the APIs.

In other embodiments, the poloxamer-based intralesional injections are employed for virotherapy treatments. In these embodiments, the poloxamer-based injections include infectious disease viruses as the therapeutic agent (e.g., the API). Further to these embodiments, the infectious disease viruses within the poloxamer-based injections are programmed to infect cancer cells or other targeted tissue.

In further embodiments, the poloxamer-based intralesional injections are employed for gene therapy. In these embodiments, the poloxamer-based intralesional injections include suitable viral vectors, such as, for example retrovirus, adenovirus, lentivirus, among others, as the therapeutic agent. In yet further embodiments, the poloxamer-based intralesional injections include suitable non-viral vectors as the therapeutic agent.

In some embodiments, the amounts of the APIs included in the poloxamer-based intralesional injections are calculated depending on the body surface area (BSA) of the patient (e.g., canine, feline, humans). In these embodiments, the amounts of the chemotherapeutic agents included in the poloxamer-based intralesional injections are calculated in mg/m2. Further to these embodiments, the amount of the poloxamers included in the poloxamer-based intralesional injections range from about 1% to about 50%; with the most suitable amounts ranging from about 5% to about 40%. These percent ranges may refer to % weight by weight, % weight by volume, or % volume by volume.

In some embodiments, the poloxamer-based intralesional injections provide a therapy response time of about three months. In these embodiments, the intralesional injections are administered once per month, during three months. Further to these embodiments, after three months of treatment with the disclosed poloxamer-based intralesional injections, the patients exhibit positive outcomes.

In other embodiments, the poloxamer-based injections can be administered using different routes of administration. Examples of the routes of administration include intralesional injections, sublesional injections, intravenous administration (IV), and the like. Further to these embodiments, the poloxamer-based injections are administered to humans or other species of animals, such as, for example, birds, mammals and reptiles.

Further aspects of the invention are provided in the following numbered paragraphs.

A composition for treating a patient with cancer comprising: an intralesional injection solution including a concentration of at least one poloxamer dissolved in a solvent; a concentration of at least one anti-cancer active pharmaceutical ingredient dissolved in said intralesional injection solution.

The composition for treating a patient with cancer wherein said anti-cancer active pharmaceutical ingredient is a chemotherapeutic agent.

The composition for treating a patient with cancer wherein said at least one chemotherapeutic agent is at least one alkylating agent selected from the group consisting of: nitrosourea, nitrogen mustards, alkyl sulfonates, thiotepa, procarbazine, altretamine, triazenes, platinum agents, and combinations thereof.

The composition for treating a patient with cancer wherein said at least one chemotherapeutic agent is selected from the group consisting of: cisplatin, carboplatin, nedaplatin, oxaliplatin, satraplatin, triplatin tetranitrate, among others; antimetabolite agents, such as, 5-fluorouracil, 6-mercaptopurine, capecitabine, cytarabine, floxuridine, fludarabine, gemcitabine, hydroxyurea, methotrexate, pemetrexed, and combinations thereof.

The composition for treating a patient with cancer wherein said at least one anti-cancer active pharmaceutical ingredient is an infectious disease virus programmed to infect the cancer.

The composition for treating a patient with cancer wherein said infectious disease virus is selected from the group consisting of retrovirus, adenovirus, lentivirus, and combinations thereof.

The composition for treating a patient with cancer wherein said concentration of said at least one anti-cancer active pharmaceutical ingredient is dependent upon the body surface area of the patient.

The composition for treating a patient with cancer wherein said at least one poloxamer is selected from the group consisting of poloxamer 407 and poloxamer 188.

The composition for treating a patient with cancer wherein said at least one poloxamer is mixture of poloxamer 407 and poloxamer 188.

The composition for treating a patient with cancer wherein said concentration of said at least one poloxamer is from about 1% to about 50%.

The composition for treating a patient with cancer wherein said concentration of said at least one poloxamer is from about 5% to about 40%

The composition for treating a patient with cancer wherein said cancer is formed of cancer cells and said at least one poloxamer is selected to inhibit the normal MDR proteins on the surface of said cancer cells.

The composition for treating a patient with cancer wherein said cancer is a tumor or carcinoma and wherein the concentration of said at least one poloxamer is a liquid upon intralesional injection and a gel following intralesional injection into said tumor or carcinoma.

A method of treating a patient with cancer comprising: preparing a solution including a concentration of at least one poloxamer dissolved in a solvent; incorporating a concentration of at least one anti-cancer active pharmaceutical ingredient into said solution; injecting said solution directly into a carcinoma or tumor of the patient wherein said carcinoma or tumor includes cancer cells.

The method of treating a cancer patient wherein said at least one anti-cancer pharmaceutical ingredient is a chemotherapeutic agent.

The method of treating a cancer patient wherein said at least one anti-cancer pharmaceutical ingredient is an infectious disease virus.

The method of treating a cancer patient wherein said infectious disease virus is programmed to infect said cancer cells.

The method of treating a cancer patient wherein said at least one poloxamer is selected to inhibit the normal MDR proteins on the surface of said cancer cells.

The method of treating a cancer patient wherein the concentration of said at last one poloxamer is a liquid upon injection and a gel following injection into said carcinoma or tumor.

The method of treating a cancer patient wherein said concentration of said at least one anti-cancer pharmaceutical ingredient is dependent upon the body surface area of the patient.

The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the method and to the arrangements of the components set forth in the following description. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

DETAILED DESCRIPTION OF THE PREFERRED EMBODIMENTS

The present disclosure is described here in detail. Other embodiments may be used and/or other changes may be made without departing from the spirit or scope of the present disclosure. The described embodiments are not meant to limit the subject matter presented here.

Definitions

As used here, the following terms have the following definitions:

"Active Pharmaceutical Ingredients (APIs)" refer to chemical compounds that induce a desired effect, and include agents that are therapeutically or prophylactically effective.

"Intralesional Injection" refers to the direct delivery of medication percutaneously into skin lesions.

"Treating" and "Treatment" refers to reduction in severity and/or frequency of symptoms, elimination of symptoms and/or underlying cause, prevention of the occurrence of symptoms and/or their underlying cause, and improvement or remediation of damage.

"Vehicle" refers to a substance of no therapeutic value that is used to convey at least one API for administration.

DESCRIPTION OF THE DISCLOSURE

The present disclosure is here described in detail with reference to embodiments. Other embodiments may be used and/or other changes may be made without departing from the spirit or scope of the present disclosure. The illustrative embodiments described in the detailed description are not meant to be limiting of the subject matter presented here.

There is a need for cancer treatments possessing fewer side effects and exhibiting the property of efficiently targeting only the cancer cells. The present invention is directed to less toxic and more efficient treatments for the following cancers: carcinoma, such as, for example, squamous cell carcinoma, adenocarcinoma, adenosquamous carcinoma, anaplastic carcinoma, large cell carcinoma, small cell carcinoma, among others; as well as other types of cancer, such as, for example, mast cell tumor, lipoma, histiocytoma, perianal gland adenoma, sebaceous gland hyperplasia adenoma, and the like.

Poloxamers are polymeric surfactants generally suitable for use as therapeutic vehicles. Preferred poloxamers for intralesional injections of the present disclosure include poloxamer 407 and poloxamer 188 as these poloxamers are known to be approved for pharmaceutical use. The published molecular weight of poloxamer 407 is 12,600 daltons and is available commercially in the molecular weight range of approximately 9840-14600 daltons. The published molecular weight of poloxamer 188 is 8,400 daltons and is available commercially in the molecular weight range of approximately 7,680-9510 daltons. Poloxamer 407 exhibits synergistic properties with poloxamer 188. Other contemplated poloxamers include, but are not limited to, poloxamers 401, 124, 234, 237, and 338. These poloxamers are commercially available from a number of sources, in particular, from BASF and Sigma-Aldrich.

As used herein the term "poloxamer" means any di- or tri-block copolymer composed of propylene oxide and ethylene oxide. Poloxamers of the Pluronic® type are tri-block copolymers in which the propylene oxide block is sandwiched between two ethylene oxide blocks and has the following general formula and structure:

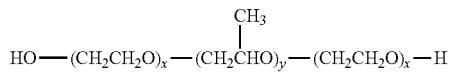

Poloxamers of the reverse Pluronic® type have the following structure:

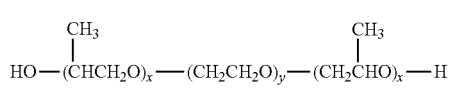

In the nomenclature of poloxamers, the non-proprietary name "poloxamer" is followed by a number, the first two digits of which, when multiplied by 100, equals the average molecular weight ("mw") of the polyoxypropylene (POP) and the third digit, when multiplied by 10 equals the approximate weight percent of the polyoxyethylene (POE). Thus, for example, poloxamer 188 would have an average POP mw of about 1800 and an average POE % of 80%. (Lorraine Reeves, Handbook of Biodegradable Polymers, Chapter 12, "The Poloxamers: Their Chemistry and Medical Applications", in Drug Targeting and Delivery Series, Vol. 7, Harwood Academic Publishers, 1997.)

The following is a table summarizes the average characteristics of some poloxamers:

| BASF* | Poloxamer | BASF mw Range | Ave. # POP units | Ave. # POE units | Wt % POE | MW POP | Formula$^R$ Formula Derived f/BASF |
|---|---|---|---|---|---|---|---|
| L44NF | Poloxamer 124 | 2200 (2090-2360) | 20 | 24.0 | 46.7 ± 1.9 | 1160 | HO—$(C_2H_4O)_{12}$—$(C_3H_6O)_{20}$—$(C_2H_4O)_{12}$—H |
| L121 | Poloxamer 401 | 4400$^R$ | 67$^R$ | 12$^R$ | 12$^R$ | 3886$^R$ | HO—$(C_2H_4O)_{6}$—$(C_3H_6O)_{67}$—$(C_2H_4O)_{6}$—H$^R$ |
| F68NF | Poloxamer 188 | 8400 (7680-9510) | 27 | 160 | 81.8 ± 1.9 | 1800 | HO—$(C_2H_4O)_{80}$—$(C_3H_6O)_{27}$—$(C_2H_4O)_{80}$—H |
| F87NF | Poloxamer 237 | 7700 (6840-8830) | 37 | 128 | 72.4 ± 1.9 | | HO—$(C_2H_4O)_{64}$—$(C_3H_6O)_{37}$—$(C_2H_4O)_{64}$—H |
| F108NF | Poloxamer 338 | 14600 (12700-17400) | 44 | 282 | 83.1 ± 1.7 | 3250 | HO—$(C_2H_4O)_{141}$—$(C_3H_6O)_{44}$—$(C_2H_4O)_{141}$—H |
| F127NF | Poloxamer 407 | 12600 (9840-14600) | 56 | 202 | 73.2 ± 1.7 | 11716 | HO—$(C_2H_4O)_{101}$—$(C_3H_6O)_{56}$—$(C_2H_4O)_{101}$—H |

*Values taken from BASF NF Grade Pluronic Polymers Technical Bulletin Sep. 17, 2001 unless indicated
$^R$Values taken from Lorraine Reeves, Handbook of Biodegradable Polymers, Chapter 12, in Drug Targeting and Delivery Series, Vol. 7, Harwood Academic Publishers, 1997.

Concentrated aqueous solutions of many poloxamers form gels. These gels may revert back to a liquid upon a decrease in temperature. With regard to the intralesional injections of the present disclosure, the reverse thermal gelation characteristics of the poloxamer(s) may be employed to provide a liquid injection composition (including an API) that may form a gel at the intralesional injection site at body temperature. In this way, the use of poloxamers in the intralesional injections of the present disclosure may provide enhanced solubility properties for the API, but may also enhance bioavailability and may reduce the therapeutic concentration of the API, by increasing the contact of the API at the intralesional injection site.

Poloxamers have been shown to preferentially target cancer cells due to differences in the membrane of the cancer cells when compared to normal cells. Poloxamers have also been shown to inhibit multiple drug resistant (MDR) proteins and other drug efflux transporters on the surface of the cancer cells; the MDR proteins are responsible for the efflux of drugs from the cells, thereby increasing the susceptibility of cancer cells to chemotherapeutic agents.

In some embodiments, intralesional injections for the treatment of cancer are disclosed. In these embodiments, the intralesional injections include at least one chemotherapeutic agent as the API within a poloxamer-based composition. Further to these embodiments, the poloxamer-based composition employed as the therapeutic vehicle includes one or more poloxamers having different molecular weights. In these embodiments, the intralesional injections include different/additional components, such as, a solvent (e.g., distilled water), among others. Further to these embodiments, the combination of the poloxamer-based composition with the chemotherapeutic agents provides a synergistic effect due to the multiple molecular weight poloxamers attraction to cells possessing abnormal membrane structures. This synergistic effect allows lower dosages of the APIs, an improved chemosensitization of cancer cells, and an increase in the cytotoxic activity of the chemotherapeutic agents on the cancer cells.

In some embodiments, the intralesional injections are composed of at least one poloxamer compound and an API. In these embodiments, the poloxamer compound is employed in liquid state and provides enhanced contact between the API and the target biological tissue. Further to these embodiments, the poloxamer compound within the intralesional injections forms a thermoreversible gel which undergoes solution-gel transition upon an increase in temperature. In these embodiments, the formed gel at the injection site remains in contact with the targeted biological tissue of the patient, thereby allowing prolonged pharmacological action of the APIs. Further to these embodiments, the formed gel provides a sustained release of the APIs resulting in an increased residence time at the injection site and improved therapeutic effectiveness.

In other embodiments, increasing the concentration of the poloxamer compounds within the intralesional injection results in a reduction of the APIs' release rate and in an extended diffusion of the APIs through the poloxamer matrix. In these embodiments, the concentration of the poloxamer compounds within the intralesional injections provides the desired delivery rate of the APIs, such as, for example a controlled release or an immediate release.

In some embodiments, the disclosed poloxamer-based intralesional injections are employed for treating a plurality of cancer in humans and animals. In these embodiments, the poloxamer-based intralesional injections can be used to effectively reduce the size of carcinomas or tumors. Further to these embodiments, the poloxamer-based injections are used to eliminate cancer from a patient.

In some embodiments, the poloxamer-based intralesional injections are applied directly into a carcinoma or tumor of a patient suffering from cancer. In these embodiments, the local therapeutic effect of the poloxamer-based intralesional injections allows lower dosages of the APIs and provides higher concentrations of the APIs at the targeted site. Further to these embodiments, the poloxamer-based intralesional injections are suitable treatments for regression of tumors and elimination of carcinomas. In these embodiments, the poloxamer-based intralesional injections allow the APIs to bypass the skin and subcutaneous tissue of the patient as well as the outer defensive abnormal tissue layers of the tumor to reach a specific target area of a patient, thereby enhancing the treatment effectiveness.

In some embodiments, the poloxamer-based intralesional injections are formulated to specifically target abnormal cells that are the cause of tumor formations or carcinomas in a patient. In these embodiments, the poloxamer vehicle within the injections is attracted to abnormal cells possessing different membrane structures than normal cells. Further to these embodiments, the poloxamer vehicle within the injections causes inhibition of the normal functioning of MDR proteins on the surface of abnormal cells. In these embodiments, the inhibition of the MDR proteins to function normally on the surface of the abnormal cells increases the effectiveness of chemotherapeutic agents in eliminating or reducing tumors and carcinomas.

In some embodiments, the poloxamer-based intralesional injections are administered alone as the sole therapeutic agent. In other embodiments, the poloxamer-based intralesional injections are used in combination with one or more additional therapies, such as, for example, radiation therapy, electrotherapy, and immunotherapy, among others.

In some embodiments, the poloxamer-based intralesional injections enable an efficient administration of the APIs, such as, for example, chemotherapeutic agents, thereby improving the safety and effectiveness of the treatment. In these embodiments, the poloxamer-based intralesional injections are used for localized delivery of the APIs. Further to these embodiments, the poloxamer-based intralesional injections allow the delivery of chemotherapeutic agents directly at the target site, such as, for example tumors or carcinomas of a patient, thereby resulting in a higher concentration of the APIs at the target site. In other embodiments, the poloxamer-based intralesional injections are used for systemic delivery of the APIs. In these embodiments, the poloxamer-based intralesional injections allow the delivery of chemotherapeutic agents to the systemic circulation, thereby resulting in a higher percentage of bioavailability of the APIs.

In some embodiments, the poloxamer-based intralesional injections are suitable for administration in tumors or carcinomas located in different sites of a patient's body. In these embodiments, the poloxamer-based intralesional injections are employed in cases of cancer in different stages of development. Further to these embodiments, the poloxamer-based intralesional injections are administered during stage 0 'in situ', stage 1 'localized cancer'; stages 2 and 3 'regional spread'; and final stage 4.

In other embodiments, the poloxamer-based intralesional injections are employed for virotherapy treatments. In these embodiments, the poloxamer-based injections include infectious disease viruses as the therapeutic agent (e.g., the API). Further to these embodiments, the infectious disease viruses within the poloxamer-based injections are programmed to infect cancer cells or other targeted tissue.

In further embodiments, the poloxamer-based intralesional injections are employed for gene therapy. In these embodiments, the poloxamer-based intralesional injections include suitable viral vectors, such as, for example retrovirus, adenovirus, lentivirus, among others, as the therapeutic agent. In yet further embodiments, the poloxamer-based intralesional injections include suitable non-viral vectors as the therapeutic agent.

Formulation

In some embodiments, the disclosed intralesional injections include at least one chemotherapeutic agent as the API within a poloxamer-based composition. In these embodiments, the poloxamer-based composition includes one or more poloxamers with different molecular weights as the therapeutic vehicle. Further to these embodiments, the intralesional injections include different/additional components, such as a solvent (e.g., distilled water), among others.

In some embodiments, the chemotherapeutic agents used to manufacture the poloxamer-based intralesional injections include: alkylating agents, such as, nitrosourea, nitrogen mustards, alkyl sulfonates, thiotepa, procarbazine, altretamine, triazenes, platinum agents, and the like; alkylating-like agents, such as, cisplatin, carboplatin, nedaplatin, oxaliplatin, satraplatin, triplatin tetranitrate, among others; antimetabolite agents, such as, 5-fluorouracil, 6-mercaptopurine, capecitabine, cytarabine, floxuridine, fludarabine, gemcitabine, hydroxyurea, methotrexate, pemetrexed, among others; and analogs, derivatives, mixtures thereof, or the like. The list of chemotherapeutic agents above is not exhaustive; other compounds described in the art that meet the set requirements can also be considered. In an example, the chemotherapeutic agent employed in the poloxamer-based intralesional injections is carboplatin. Such chemotherapeutic agents are commercially available from a number of sources such as Astra Zeneca, Eli Lilly & Co, Glaxo Smithkline, Hoffman-La Roche, Johnson-Matthey; Merck & Co. and Schering AG.

In some embodiments, the amounts of the APIs included in the poloxamer-based intralesional injections are calculated depending on the body surface area (BSA) of the patient (e.g., canine, feline, humans). In these embodiments, the amounts of the chemotherapeutic agents included in the poloxamer-based intralesional injections are calculated in mg/m2. In an example, when the patient is a canine, the amount of the chemotherapeutic agents included in the poloxamer-based intralesional injections is of about 350 mg/m2. In another example, when the patient is a feline, the amount of the chemotherapeutic agents included in the poloxamer-based intralesional injections is of about 240 mg/m2.

In some embodiments, the poloxamer-based intralesional injections include one or more poloxamer compounds. In these embodiments, the mixture of the poloxamer compounds results in a liquid solution which provides enhanced contact between the injection and the target biological tissue. Further to these embodiments, the poloxamer compounds include a variety of poloxamers with different molecular weights. In an example, the poloxamer employed in the disclosed intralesional injections is poloxamer 407. In another example, the poloxamer employed in the disclosed intralesional injections is poloxamer 188. In a further example, the mixture of poloxamers employed in the disclosed intralesional injections includes poloxamer 407 and poloxamer 188.

In some embodiments, the amount of the poloxamers included in the poloxamer-based intralesional injections range from about 1% to about 50%; with the most suitable amounts ranging from about 5% to about 40%. These percent ranges may refer to % weight by weight, % weight by volume, or % volume by volume.

Administration

In some embodiments, the poloxamer-based intralesional injections provide a therapy response time of about three months. In these embodiments, the intralesional injections are administered once per month, during three months. Further to these embodiments, after three months of treatment with the disclosed poloxamer-based intralesional injections, the patients exhibit positive outcomes.

In some embodiments, the poloxamer-based intralesional injections are manufactured to deliver a specific dosage of an active drug to a patient. In these embodiments, the required dosages, dosing frequency, and period of treatment will depend on the type of cancer, size of the tumor or carcinoma, and the type of chemotherapeutic agent included in the disclosed intralesional injection. In other words, some chemotherapeutic agents are more potent than others and some are used to treat certain types of cancer; hence, the dosage regimen can be adjusted as needed for the type of cancer as recommended by a physician.

In other embodiments, the poloxamer-based injections can be administered using different routes of administration. Examples of the routes of administration include intralesional injections, sublesional injections, intravenous administration (IV), and the like. Further to these embodiments, the poloxamer-based injections are administered to humans or other species of animals, such as, for example, birds, mammals and reptiles.

EXAMPLE

As an example, a sun bear suffering from squamous cell carcinoma in the oral cavity is identified. The sun bear is sedated before administration of the disclosed poloxamer-based intralesional injection.

The sun bear suffering from squamous cell carcinoma in the oral cavity is injected with the intralesional injection of the present disclosure according to an embodiment. In this embodiment, a suitable amount of the disclosed poloxamer-based intralesional injection is administered by injection directly into the squamous cell carcinoma. In this embodiment, the disclosed intralesional injection includes poloxamer 407, carboplatin, and distilled water. The treatment may be repeated, as necessary, such as monthly, until the carcinoma is eradicated.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Thus, the present invention is well adapted to carry out the objects and attain the ends and advantages mentioned above as well as those inherent therein. While the inventive device has been described and illustrated herein by reference to certain preferred embodiments, various changes and further modifications, apart from those shown or suggested herein, may be made therein by those of ordinary skill in the art, without departing from the spirit of the inventive concept the scope of which is to be determined by the following claims.

What is claimed is:

1. A composition for treating a patient with one or more of lung cancer, blood cancer, brain cancer, perianal gland adenoma, squamous cell carcinoma, mast cell tumor, lipoma, histiocytoma, sebaceous gland hyperplasia adenoma, adenocarcinoma, adenosquamous carcinoma, anaplastic carcinoma, large cell carcinoma, and small cell carcinoma, the composition comprising:
   an intralesional injection solution including a concentration of at least one poloxamer dissolved in a solvent;
   a concentration of at least one anti-cancer active pharmaceutical ingredient dissolved in said intralesional injection solution.

2. The composition of claim 1 wherein said at least one anti-cancer active pharmaceutical ingredient comprises a chemotherapeutic agent.

3. The composition of claim 2 wherein said at least one chemotherapeutic agent comprises at least one alkylating agent selected from the group consisting of: nitrosourea, nitrogen mustards, alkyl sulfonates, thiotepa, procarbazine, altretamine, triazenes, platinum agents, and combinations thereof.

4. The composition of claim 2 wherein said at least one chemotherapeutic agent comprises at least one agent selected from the group consisting of: cisplatin, carboplatin, nedaplatin, oxaliplatin, satraplatin, and triplatin tetranitrate, 5-fluorouracil, 6-mercaptopurine, capecitabine, cytarabine, floxuridine, fludarabine, gemcitabine, hydroxyurea, methotrexate, pemetrexed, and combinations thereof.

5. The composition of claim 1 wherein said at least one anti-cancer active pharmaceutical ingredient comprises an infectious disease virus programmed to infect the cancer.

6. The composition of claim 5 wherein said infectious disease virus is selected from the group consisting of retrovirus, adenovirus, lentivirus, and combinations thereof.

7. The composition of claim 1 wherein said concentration of said at least one anti-cancer active pharmaceutical ingredient is dependent upon the body surface area of the patient.

8. The composition of claim 1 wherein said at least one poloxamer is selected from the group consisting of poloxamer 407 and poloxamer 188, and combinations thereof.

9. The composition of claim 8 wherein said at least one poloxamer is mixture of poloxamer 407 and poloxamer 188.

10. The composition of claim 1 wherein said concentration of said at least one poloxamer is from about 1% to about 50%.

11. The composition of claim 1 wherein said concentration of said at least one poloxamer is from about 5% to about 40%.

12. The composition of claim 1 wherein said cancer is formed of cancer cells and said at least one poloxamer is selected to inhibit the normal MDR proteins on the surface of said cancer cells.

13. The composition of claim 1 wherein said cancer is a tumor or carcinoma and wherein the concentration of said at least one poloxamer is a liquid upon intralesional injection and a gel following intralesional injection into said tumor or carcinoma.

14. A method for use in the treatment of one or more of lung cancer, blood cancer, brain cancer, perianal gland adenoma, squamous cell carcinoma, mast cell tumor, lipoma, histiocytoma, sebaceous gland hyperplasia adenoma, adenocarcinoma, adenosquamous carcinoma, anaplastic carcinoma, large cell carcinoma, and small cell carcinoma, the method comprising:
  preparing a solution including a concentration of at least one poloxamer dissolved in a solvent;
  incorporating a concentration of at least one anti-cancer active pharmaceutical ingredient into said solution;
  injecting said solution directly into a carcinoma or tumor of a patient wherein said carcinoma or tumor includes cancer cells.

15. The solution for use in the treatment of cancer of claim 14 wherein said at least one anti-cancer pharmaceutical ingredient comprises a chemotherapeutic agent.

16. The solution for use in the treatment of cancer of claim 14 wherein said at least one anti-cancer pharmaceutical ingredient is an infectious disease virus.

17. The solution for use in the treatment of cancer of claim 16 wherein said infectious disease virus is programmed to infect said cancer cells.

18. The solution for use in the treatment of cancer of claim 14 wherein said at least one poloxamer is selected to inhibit the normal MDR proteins on the surface of said cancer cells.

19. The solution for use in the treatment of cancer of claim 14 wherein the concentration of said at last one poloxamer is a liquid upon injection and a gel following injection into said carcinoma or tumor.

20. The solution for use in the treatment of cancer of claim 14 wherein said concentration of said at least one anti-cancer pharmaceutical ingredient is dependent upon the body surface area of the patient.

* * * * *